United States Patent
Jinkerson et al.

(10) Patent No.: US 7,803,359 B1
(45) Date of Patent: Sep. 28, 2010

(54) UV-ABSORBERS FOR OPHTHALMIC LENS MATERIALS

(75) Inventors: David L. Jinkerson, Benbrook, TX (US); Joseph I. Weinschenk, III, Fort Worth, TX (US); W. Dennis Dean, Burleson, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 12/435,975

(22) Filed: May 5, 2009

Related U.S. Application Data

(60) Provisional application No. 61/050,811, filed on May 6, 2008.

(51) Int. Cl.
*C07D 249/16* (2006.01)
*C07D 249/18* (2006.01)
*C07D 249/20* (2006.01)
*C07D 249/22* (2006.01)
*C07D 255/04* (2006.01)

(52) U.S. Cl. .................... 424/78.04; 548/259; 548/256

(58) Field of Classification Search ........................ None
See application file for complete search history.

(56) References Cited

U.S. PATENT DOCUMENTS

| | | | |
|---|---|---|---|
| 4,716,234 A | 12/1987 | Dunks et al. | |
| 4,803,254 A | 2/1989 | Dunks et al. | |
| 5,290,892 A | 3/1994 | Namdaran et al. | |
| 5,331,073 A | 7/1994 | Weinschenk, III et al. | |
| 5,455,152 A * | 10/1995 | Vishwakarma | 430/512 |
| 5,470,932 A | 11/1995 | Jinkerson | |
| 5,543,504 A | 8/1996 | Jinkerson | |
| 5,637,726 A | 6/1997 | Collins et al. | |
| 5,693,095 A | 12/1997 | Freeman et al. | |
| 6,166,218 A | 12/2000 | Ravichandran et al. | |
| 6,528,602 B1 | 3/2003 | Freeman et al. | |
| 6,806,337 B2 | 10/2004 | Schlueter et al. | |
| 6,846,897 B2 | 1/2005 | Salamone et al. | |
| 6,852,793 B2 | 2/2005 | Salamone et al. | |
| 6,872,793 B1 | 3/2005 | Schlueter et al. | |
| 7,037,954 B2 | 5/2006 | Baba et al. | |
| 7,067,602 B2 | 6/2006 | Benz et al. | |
| 7,101,949 B2 | 9/2006 | Salamone et al. | |
| 7,326,423 B2 | 2/2008 | Pearson et al. | |
| 2006/0252850 A1 | 11/2006 | Jani et al. | |
| 2007/0092830 A1 | 4/2007 | Lai et al. | |
| 2007/0092831 A1 | 4/2007 | Lai et al. | |
| 2008/0242818 A1 | 10/2008 | Benz et al. | |
| 2008/0266519 A1 | 10/2008 | Schlueter | |
| 2009/0043007 A1 | 2/2009 | Weinschenk, III et al. | |
| 2009/0043105 A1 | 2/2009 | Weinschenk, III et al. | |

FOREIGN PATENT DOCUMENTS

| | | |
|---|---|---|
| CN | 1727338 | 2/2006 |
| EP | 1033590 B1 | 5/2008 |
| JP | 2005053058 | 3/2005 |
| JP | 2009013148 | 1/2009 |
| WO | WO2008109624 A2 | 9/2008 |

OTHER PUBLICATIONS

Takakis, et al., "Preparation of Benzofuroxans and Benzofurazans of 2,3,4,5-Tetrahydrobenzo[b][1.4]dioxocin and Related Compounds," J. Heterocyclic Chem., 1990, pp. 177-181, vol. 27.

\* cited by examiner

*Primary Examiner*—Kamal A Saeed
*Assistant Examiner*—Michael Barker
(74) *Attorney, Agent, or Firm*—Patrick M. Ryan

(57) ABSTRACT

UV absorbing compounds that are particularly useful in ophthalmic devices are disclosed.

18 Claims, 2 Drawing Sheets

UV-Visible Transmission spectra for Compounds A – F and 1 - 3 in Acrylic Lens Material Slabs UV-Visible Transmission spectra for Compound 1 in Acrylic Lens Material Slabs
Before and After Extraction UV-Visible Transmission spectra for Compound 1 in Acrylic Lens Material Slabs
Before and After Extraction

UV-ABSORBERS FOR OPHTHALMIC LENS MATERIALS

CROSS-REFERENCE TO RELATED APPLICATIONS

This application claims priority U.S. Provisional Patent Application No. 61/050,811, filed May 6, 2008, the entire contents of which are incorporated herein by reference.

FIELD OF THE INVENTION

This invention is directed to ophthalmic lens materials. In particular, this invention relates to ultraviolet light absorbers that are suitable for use in ophthalmic lens materials.

BACKGROUND OF THE INVENTION

Many UV light absorbers are known as ingredients for polymeric materials used to make ophthalmic lenses and, in particular, intraocular lenses. UV absorbers are preferably covalently bound to the polymeric network of the lens material instead of simply physically entrapped in the material to prevent the absorber from migrating, phase separating or leaching out of the lens material. Such stability is particularly important for implantable ophthalmic lenses where the leaching of the UV absorber may present both toxicological issues and lead to the loss of UV blocking activity in the implant.

Numerous copolymerizable benzotriazole, benzophenone and triazine UV absorbers are known. Many of these UV absorbers contain conventional olefinic polymerizable groups, such as methacrylate, acrylate, methacrylamide, acrylamide or styrene groups. Copolymerization with other ingredients in the lens materials, typically with a radical initiator, incorporates the UV absorbers into the resulting polymer chain. Incorporation of additional functional groups on a UV absorber may influence one or more of the UV absorber's UV absorbing properties, solubility or reactivity. If the UV absorber does not have sufficient solubility in the remainder of the ophthalmic lens material ingredients or polymeric lens material, the UV absorber may coalesce into domains that could interact with light and result in decreased optical clarity of the lens.

Examples of polymeric ophthalmic lens materials that incorporate UV absorbers can be found in U.S. Pat. Nos. 5,290,892; 5,331,073 and 5,693,095.

In addition to blocking UV light, some ophthalmic lenses also block blue light. See, for example, U.S. Pat. Nos. 5,470,932 and 5,543,504. These lenses block both types of light by using two chromophores: a UV absorber and a yellow dye.

There is a need for UV absorbers that are suitable for use in implantable ophthalmic lenses and are capable of blocking not only UV light (400 nm and below) but also blocking at least some light between 400-450 nm.

SUMMARY OF THE INVENTION

The present invention provides UV absorbers that block not only UV light but also light in the 400-450 nm range. These UV absorbers are suitable for use in ophthalmic devices, including contact lenses, and are particularly useful in implantable lenses, such as intraocular lenses (IOLs). The UV absorbers of the present invention are copolymerizable with other ingredients in ophthalmic device formulations.

DETAILED DESCRIPTION OF THE INVENTION

Figure 1:
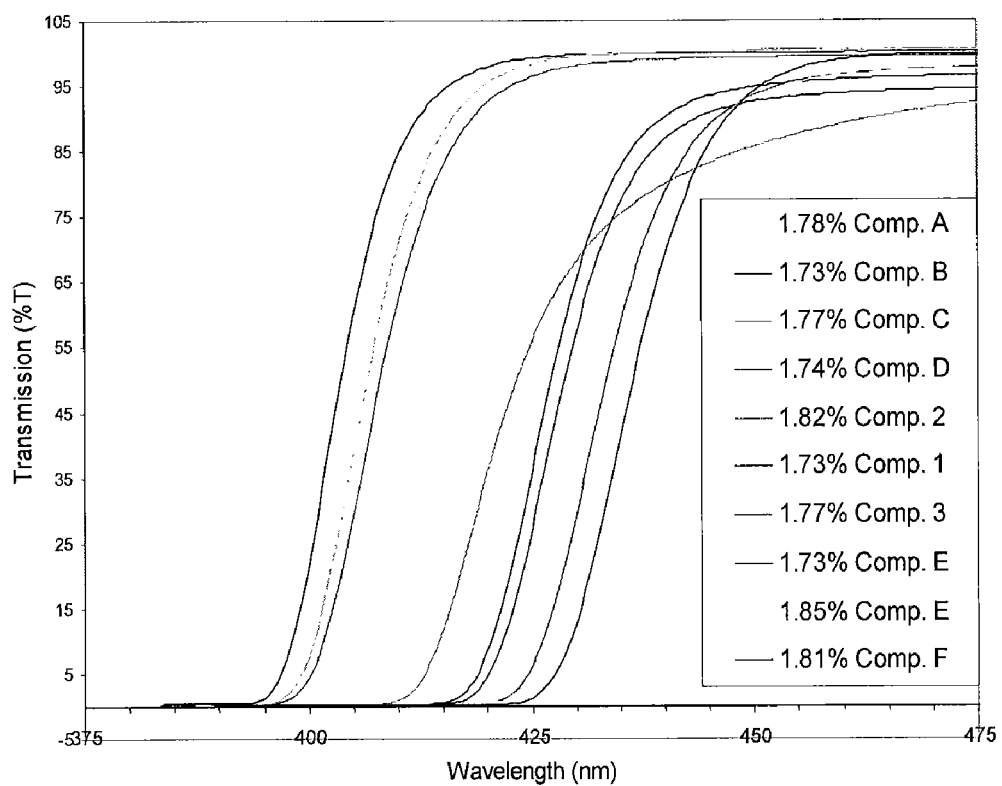
FIG. 1 shows the UV/VIS spectra of various UV absorbers.

Unless indicated otherwise, all ingredient amounts expressed in percentage terms are presented as % w/w.

The UV absorbers of the present invention have the structure shown in formula I.

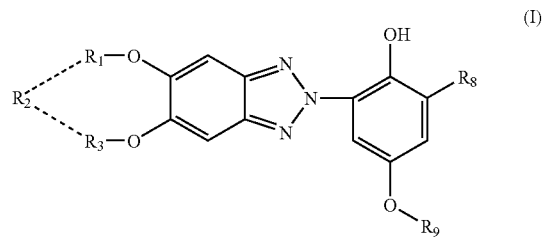

wherein $R_1$ and $R_3$ independently=H; $C_1$-$C_{12}$ alkyl, optionally substituted; $C_1$-$C_{12}$ cycloalkyl, optionally substituted; phenyl, optionally substituted; or naphthyl; or $R_1$ and $R_3$ are linked through the optional (as designated by the dashed bonds) linking group $R_2$ where $R_2$ is a $C_1$-$C_6$ alkylene, optionally substituted; or $R_1$, $R_2$, and $R_3$ taken together form an optionally substituted 1,2-phenyl, 1,2-naphthyl, or 2,3-naphthyl, wherein, in each case, the optional substituents are independently $C_1$-$C_6$ alkyl, $C_1$-$C_6$ alkoxy, OH, —Si(CH$_3$)$_3$, halogen, —(CH$_2$CH$_2$O)$_n$—R$_{10}$, or —(CH$_2$CH(CH$_3$)O)$_n$R$_{10}$;

$R_{10}$=H, —Si(CH$_3$)$_3$, or $C_1$-$C_6$ alkyl;

$R_8$=H or $C_1$-$C_{12}$ alkyl; and $R_9$=H; $C_1$-$C_{12}$ alkyl, optionally substituted with OH; or

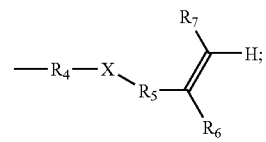

$R_4$=$C_1$-$C_{12}$ alkylene, (CH$_2$CH$_2$O)$_n$, (CH$_2$CH(CH$_3$)O)$_n$, or CH$_2$CH$_2$CH$_2$(Si(CH$_3$)$_2$O)$_m$Si(CH$_3$)$_2$CH$_2$CH$_2$CH$_2$;

X=nothing, O, NR$_7$, or S, provided that if $R_4$ is (CH$_2$CH$_2$O)$_n$, or (CH$_2$CH(CH$_3$)O)$_n$ then X is nothing;

$R_5$=nothing, C(=O), C(=O)C$_j$H$_{2j}$, $C_1$-$C_6$ alkylene, phenyl, or $C_1$-$C_6$ alkylphenyl; C(=O)O, C(=O)OC$_j$H$_{2j}$, C(=O)NR$_7$, C(=O)NR$_7$C$_j$H$_{2j}$, C(=S)O, C(=S)OC$_j$H$_{2j}$, C(=S)NR$_7$, C(=S)NR$_7$C$_j$H$_{2j}$;

n=2-10;

j=1-6;

m=1-9;

$R_6$=H or methyl; and $R_7$=H, $C_1$-$C_6$ alkyl, or phenyl.

Preferred compounds of formula (I) are those wherein:

$R_1$ and $R_3$ independently=$C_1$-$C_4$ alkyl or phenyl;

$R_2$=nothing;

$R_9=$

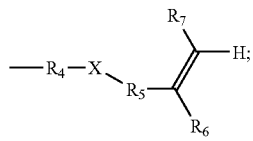

$R_4$ is $C_1$-$C_6$ alkylene;
$X$ is O or $NR_7$;
$R_5$ is C(=O) or $C_1$-$C_6$ alkylphenyl;
$R_6$ is H or methyl;
$R_7$ is H; and
$R_8$ is $C_4$-$C_{12}$ t-alkyl.

Most preferred compounds of formula (I) are those wherein:
$R_1$ and $R_3$=methyl;
$R_2$=nothing;
$R_9=$

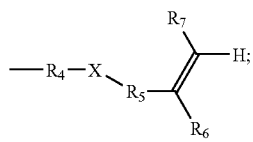

$R_4$ is $C_2$-$C_3$ alkylene;
X is O;
$R_5$ is C(=O);
$R_6$ is H or methyl;
$R_7$ is H; and
$R_8$ is t-butyl.

Compounds of formula (I) can be prepared using methods known in the art. For example, a synthetic pathway to prepare the dialkoxy/diaryloxy benzotriazoles of the present invention is shown in Scheme 1. This process starts with the diazotization reaction of the dialkoxy/diaryloxy-substituted 2-nitroaniline compound (II) to form the diazonium salt (III). The diazonium salt intermediate is immediately reacted with the target phenolic compound (IV) via azo coupling reaction to make nitro azo intermediate compound (V), which can be isolated and purified or often used in crude form. The azo coupling step is followed by the reduction of the nitro azo intermediate (V) with alkaline glucose solution and zinc powder, which closes the triazole ring providing the desired dialkoxy/diaryloxy benzotriazole compound (VI).

Scheme 1
Generic 2-hydroxyphenyl-
5,6-dialkoxy/diaryloxy-2H-benzotriazole synthesis

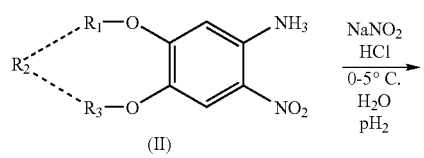

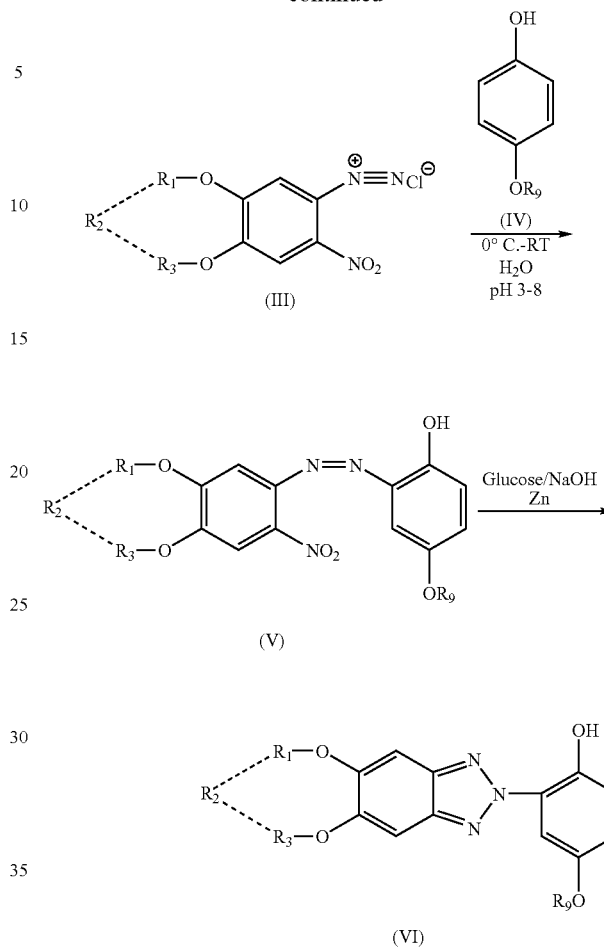

In general, reaction scheme 1 works best when $R_9$ does not contain an ester, carbonate, carbamate, or isocyanate group. In those cases, the polymerizable group (containing an ester, carbonate, carbamate, or isocyanate group) should be added after the scheme 1 reaction sequence. For example, if $R_9$ included an ester group, such as the case when $R_9$ is an acrylate or methacrylate group, the phenolic reactant (IV) may have an omega-chain hydroxyl alkylene group (e.g., —$CH_2CH_2OH$) in place of the desired $R_9$ group during the reaction sequence of scheme 1. The desired $R_9$ group could then be added via a dehydrohalogenation reaction using acryloyl- or methacryloyl-chloride, for example.

In general, the specialty dialkoxy/diaryloxy-substituted 2-nitroanilines, denoted as (II) in Scheme 1 above, as well as, the specialty target phenolic compound (IV), may be synthesized by methods and techniques known to those skilled in the art. For example, the synthesis of a dimethoxy-substituted 2-nitroaniline is shown in Scheme 2. The 4,5-dimethoxy-2-nitroaniline can be prepared by the nitration of 4-amino veratrole (VII, Aldrich Chemical Co., a.k.a. 3,4-dimethoxyaniline) to provide the dimethoxy-substituted ortho-nitroaniline (VIII) starting material needed for the benzotriazole synthesis (Scheme 1).

Scheme 2
Specific Synthetic Pathway to
Prepare 4,5-dimethoxy-2-nitroaniline Starting Material (II)

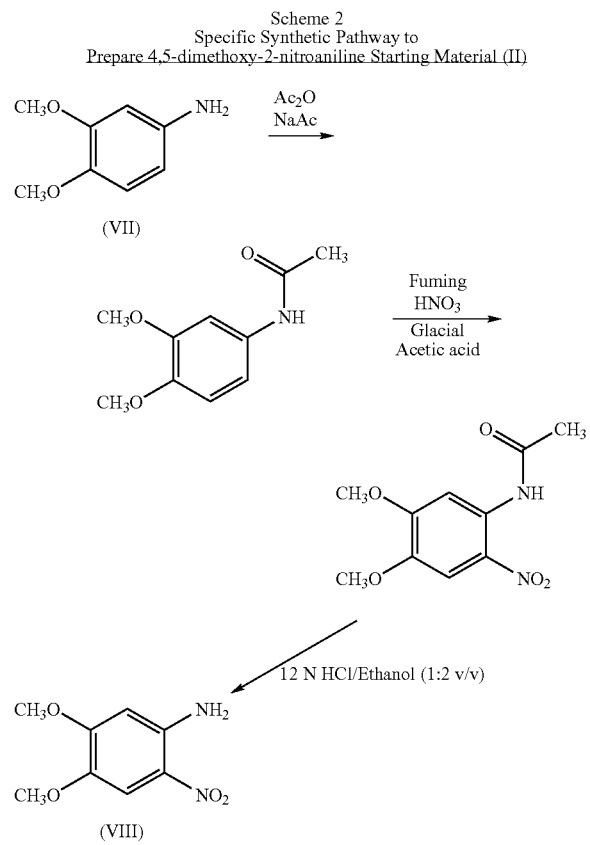

The UV absorbers of the present invention are particularly suitable for use in IOLs. IOL materials will generally contain from 0.1 to 5% (w/w) of a UV absorber of formula I. Preferably, IOL materials will contain from 0.1 to 2% (w/w) of a UV absorber of the present invention.

Ophthalmic device materials are prepared by copolymerizing the UV absorbers of the present invention with other ingredients, such as device-forming materials, cross-linking agents, and blue-light blocking chromophores.

Many device-forming monomers are known in the art and include both acrylic and silicone-containing monomers among others. See, for example, U.S. Pat. Nos. 7,101,949; 7,067,602; 7,037,954; 6,872,793 6,852,793; 6,846,897; 6,806,337; 6,528,602; and 5,693,095. In the case of IOLs, any known IOL device material is suitable for use in the compositions of the present invention. Preferably, the ophthalmic device materials comprise an acrylic or methacrylic device-forming monomer. More preferably, the device-forming monomers comprise a monomer of formula II:

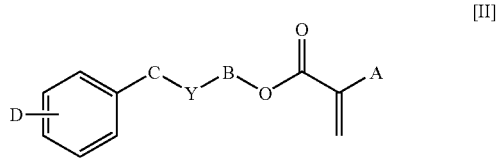

[II]

where in formula [II]:
A is H, $CH_3$, $CH_2CH_3$, or $CH_2OH$;
B is $(CH_2)_m$ or $[O(CH_2)_2]_z$;
C is $(CH_2)_w$;
m is 2-6;
z is 1-10;
Y is nothing, O, S, or NR', provided that if Y is O, S, or NR', then B is $(CH_2)_m$;
R' is H, $CH_3$, $C_{n'}H_{2n'+1}$ (n'=1-10), iso-$OC_3H_7$, $C_6H_5$, or $CH_2C_6H_5$;
w is 0-6, provided that m+w≦8; and
D is H, $C_1$-$C_4$ alkyl, $C_1$-$C_4$ alkoxy, $C_6H_5$, $CH_2C_6H_5$ or halogen.

Preferred monomers of formula II are those wherein A is H or $CH_3$, B is $(CH_2)_m$, m is 2-5, Y is nothing or O, w is 0-1, and D is H. Most preferred are 2-phenylethyl methacrylate; 4-phenylbutyl methacrylate; 5-phenylpentyl methacrylate; 2-benzyloxyethyl methacrylate; and 3-benzyloxypropyl methacrylate; and their corresponding acrylates.

Monomers of formula II are known and can be made by known methods. For example, the conjugate alcohol of the desired monomer can be combined in a reaction vessel with methyl methacrylate, tetrabutyl titanate (catalyst), and a polymerization inhibitor such as 4-benzyloxy phenol. The vessel can then be heated to facilitate the reaction and distill off the reaction by-products to drive the reaction to completion. Alternative synthesis schemes involve adding methacrylic acid to the conjugate alcohol and catalyzing with a carbodiimide or mixing the conjugate alcohol with methacryloyl chloride and a base such as pyridine or triethylamine.

Device materials generally comprise a total of at least about 75%, preferably at least about 80%, of device-forming monomers.

In addition to a UV absorber of formula I and a device-forming monomer, the device materials of the present invention generally comprise a cross-linking agent. The cross-linking agent used in the device materials of this invention may be any terminally ethylenically unsaturated compound having more than one unsaturated group. Suitable cross-linking agents include, for example: ethylene glycol dimethacrylate; diethylene glycol dimethacrylate; allyl methacrylate; 1,3-propanediol dimethacrylate; 2,3-propanediol dimethacrylate; 1,6-hexanediol dimethacrylate; 1,4-butanediol dimethacrylate; $CH_2$=$C(CH_3)C$(=O)O—($CH_2CH_2$O$)_p$—C(=O)C($CH_3$)=$CH_2$ where p=1-50; and $CH_2$=$C(CH_3)C$(=O)O($CH_2)_tO$—C(=O)C($CH_3$)=$CH_2$ where t=3-20; and their corresponding acrylates. A preferred cross-linking monomer is $CH_2$=$C(CH_3)C$(=O)O—($CH_2CH_2O)_p$—C(=O)C($CH_3$)=$CH_2$ where p is such that the number-average molecular weight is about 400, about 600, or about 1000.

Generally, the total amount of the cross-linking component is at least 0.1% by weight and, depending on the identity and concentration of the remaining components and the desired physical properties, can range to about 20% by weight. The preferred concentration range for the cross-linking component is 0.1-17% (w/w).

Suitable polymerization initiators for device materials containing a UV absorber of the present invention include thermal initiators and photoinitiators. Preferred thermal initiators include peroxy free-radical initiators, such as t-butyl (peroxy-2-ethyl)hexanoate and di-(tert-butylcyclohexyl) peroxydicarbonate (commercially available as Perkadox® 16 from Akzo Chemicals Inc., Chicago, Ill.). Initiators are typically present in an amount of about 5% (w/w) or less. Because free-radical initiators do not become chemically a part of the polymers formed, the total amount of initiator is customarily not included when determining the amounts of other ingredients.

The device materials containing a UV absorber of the present invention may also contain a reactive colorant. Suitable reactive blue-light absorbing compounds include those described in U.S. Pat. No. 5,470,932. Blue-light absorbers are typically present in an amount from about 0.01-0.5% (weight).

IOLs constructed of the materials of the present invention can be of any design capable of being rolled or folded into a small cross section that can fit through a relatively smaller incision. For example, the IOLs can be of what is known as a one piece or multipiece design, and comprise optic and haptic components. The optic is that portion which serves as the lens. The haptics are attached to the optic and hold the optic in its proper place in the eye. The optic and haptic(s) can be of the same or different material. A multipiece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

In addition to IOLs, the materials of the present invention are also suitable for use in other ophthalmic devices, such as contact lenses, keratoprostheses, and corneal inlays or rings.

The invention will be further illustrated by the following examples, which are intended to be illustrative, but not limiting.

Example 1

Synthesis of N-2-[2'-Hydroxy-3'-tert-butyl-5'-(3"-methacryloyloxypropoxy)phenyl]-5,6-dimethoxy-2H-benzotriazole Compound 1 a. Preparation of Starting Material 4,5-dimethoxy-2-nitroaniline

In general, the reaction schemes 1 and 2 shown above, may be applied to this specific synthetic sequence. Beginning with Scheme 2, 10 grams (65.28 mmoles) of 4-amino veratrole (Scheme 2, structure VII, a.k.a. 3,4-dimethoxyaniline, Aldrich Chemical Co.) was dissolved in 20 grams of glacial acetic acid in a 100 mL round bottomed flask. To the flask was added 22 grams of ice followed by the dropwise addition of 1.1 equivalents of acetic anhydride (7.3 grams, Aldrich Chemical Co.) with stirring via an addition funnel over a 30 minute time interval. The reaction to make the acetamide intermediate of 4-aminoveratrole occurred with the evolution of heat after which the reaction flask was placed into a water bath and heated for an hour at 55° C. The stirring was continued overnight. The 4-acetamidoveratrole product was not isolated, but the next reaction step was continued by the addition of 5.9 grams of nitric acid in 8 mL of water and the reaction was cooled to 15° C. in an ice-water bath. As the nitration reaction preceded the purple colored reaction solution turned to a red-orange color. The reaction flask was cooled in a refrigerator overnight and a red-orange powder precipitated from the solution.

The solid was filtered off and washed with 100 mL of cold water and air dried on the filter. The solid from the previous step was placed into a 100 mL round bottomed flask and 50 mL of water and a solution of 5.9 grams of potassium hydroxide (1.5 equivalents) in 14 mL of water was added to the flask. A reflux condenser was attached to the flask and the mixture was heated to boiling and refluxed overnight. From the reaction flask was cooled in ice and an orange solid precipitated from solution. The solid was filtered off, washed with 200 mL of cold water, and dried in air and overnight in a vacuum oven at 50° C. to obtain 10.0 grams (50.5 mmoles) of 4,5-dimethoxy-2-nitroaniline (VIII), 77% yield, and mp 197-199° C.

b. Preparation of Intermediate 2-tert-butyl-4-(3"-hydroxypropoxy)-6-(2'''-nitro-4''',5'''-dimethoxyphenylazo)phenol A mixture of 10.0 grams (50.5 mmoles) of 4,5-dimethoxy-2-nitroaniline (VIII) and 20 mL of concentrated hydrochloric acid was stirred overnight at room temperature in a 100 mL round bottomed flask, and diluted with 18 mL of water and 30 grams of ice. A solution of 4.16 grams of sodium nitrite in 15 mL of water was added dropwise to the reaction flask after cooling down from about −5 to 0° C. After the addition was finished, the diazonium salt mixture was stirred for 1 hour at 0° C. Sulfamic acid was added to destroy excess nitrous acid until testing with KI/Starch paper gave a negative result. The mixture was filtered and the filtrate was added dropwise to a stirred solution of 1.13 grams (50.5 mmole) of 2-tert-butyl-4-(3'-hydroxypropoxy)phenol in a 500 mL jacketed flask in a solution that contained 6.0 grams of sodium hydroxide dissolved in 200 mL of water at about −5 to. 0° C. The temperature of the jacketed flask was maintained using a circulating cooling bath by circulating a 50:50 water:ethylene glycol mixture. After approximately ⅓ of the diazonium salt solution was added, 40 mL of 10% NaOH aqueous solution was added dropwise together to the reaction mixture. Both additions ended at approximately the same time. During the additions, the reaction mixture was kept below 0° C. The reaction mixture was further stirred below 0° C. for 2 hours, then allowed to warm up to room temperature. The nitro azo intermediate was isolated by acidification with hydrochloric acid, filtration, and washing with water, then used without further purification.

c. Preparation of Intermediate N-2-[2'-Hydroxy-3'-tert-butyl-5'-(3"-hydroxypropoxy)-phenyl]-5,6-dimethoxy-2H-benzotriazole The nitro azo intermediate above from Section b, was dissolved in 150 mL of reagent ethanol in a 500 mL round bottomed flask equipped with a magnetic stirbar. A glucose solution (18.0 g, (100 mmoles) in 150 mL of aqueous 2N NaOH) was added dropwise to the nitro azo intermediate solution under nitrogen, at room temperature. The reaction temperature was kept below 30° C. by means of a water bath. The mixture was stirred overnight. Freshly activated (acid washed) zinc dust (16.5 grams) was added to the homogeneous reaction mixture. The mixture was stirred at room temperature for 2 hours and heated with a water bath at 50° C. for 1 hour. Afterwards the reaction mixture was further diluted with 100 mL of water. After 15 minutes, the stirring was discontinued and the mixture was allowed to stand for 1 hour. The resulting precipitate was separated by filtration and washed with water. The filter cake was extracted with hot reagent alcohol (total 200 mL) until only zinc remained in the solid residue. The extract was cooled to room temperature. The resulting crystals were separated by filtration, washed with cold reagent alcohol and dried under vacuum to give 6.78 g of crude benzotriazole product. The crude product was dissolved in 400 mL of boiling heptane and the resulting solution was filtered. From the solution>98% pure material (HPLC) was obtained, Yield 6.0 grams (14.9 mmoles, 29.5%).

d. Preparation of Monomer N-2-[2'-Hydroxy-3'-tert-butyl-5'-(3"-methacryloyloxypropoxy)phenyl]-5,6-dimethoxy-2H-benzotriazole In a 250 mL 3-neck round bottomed flask equipped with a magnetic stirbar, a thermometer and an addition funnel, with a pressure-equalizing side arm, were placed 6.0 grams (14.9 mmoles) of the benzotriazole of section c above, 120 mL of dry toluene, and 1.5 mL (18.5 mmole) of dry pyridine. A solution of 2.03 grams (19.4 mmoles) of methacryloyl chloride in 10 mL of toluene was added to the mixture over 30 minute time interval. The reaction mixture was stirred overnight at ambient temperature (<25° C.). A white precipitate (pyridinium chloride) was separated by filtration and washed with toluene. The filtrate and washings were combined, washed with 1N hydrochloric acid, water, aqueous sodium bicarbonate and water successively (100 mL portions of each). The organic (toluene) layer was separated from the last washing, transferred into a 250 mL flask, and then dried for 3 hours over anhydrous sodium sulfate. The sodium sulfate was filtered off and the organic layer was concentrated under vacuum by evaporation of toluene on a rotary evaporator. The residue (~6.6 grams) was dissolved in a mixture of 150 mL of methanol and 75 mL of methylene chloride by heating in a water bath at 45° C. The resulting solution was filtered to remove a small amount of insoluble material and diluted with 40 mL of methanol. The solution was cooled slowly to room temperature, then in a refrigerator and finally placed in a freezer where the temperature was lowered to about −5° C. The resulting crystals were separated by filtration, washed with 35 mL of cold methanol/methylene chloride (90/10 v/v) and dried in under vacuum to give 6.2 grams of >98% pure product (HPLC).

Example 2

UV-Visible Transmission of Solutions of Dialkoxy Benzotriazole Compounds

Solutions containing from 1.70 to as much as 1.85% by weight of the benzotriazole compounds listed in Table 1 below were prepared in either chloroform ($CHCl_3$) or dichloromethane ($CH_2Cl_2$). The solutions were prepared by dissolving about 0.018 grams of UV absorber into about 0.982 grams of solvent by weighing to an accuracy of ±0.01 mg. The UV-visible transmission spectrum of each solution was measured. The measurement was performed from 850 to 250 nm in 1-mm quartz cuvettes using a Perkin-Elmer Lambda 35 UV-Visible Spectrophotometer. The results are shown in FIG. 1. From each spectrum, the wavelengths for the 1% T and 10% T cutoff were determined and those values are listed in Table 2.

TABLE 1

| Compound | Structure |
|---|---|
| 1 | [Structure of 5,6-dimethoxy-benzotriazole linked to hydroxy-tert-butyl-phenyl with methacryloyloxypropoxy group] |
| 2 | [Structure of 5,6-dimethoxy-benzotriazole linked to hydroxy-methoxyphenyl] |
| 3 | [Structure of 5,6-dimethoxy-benzotriazole linked to hydroxy-tert-butyl-phenyl with hydroxypropoxy group] |
| A | [Structure of 5,6-dimethoxy-benzotriazole linked to hydroxy-methylphenyl] |

TABLE 1-continued

| Compound | Structure |
|---|---|
| B | 2-(5,6-dimethoxy-2H-benzotriazol-2-yl)-6-tert-butyl-4-methylphenol |
| C | 2-(5-methoxy-2H-benzotriazol-2-yl)-6-tert-butyl-4-(3-(methacryloyloxy)propyl)phenol |
| D | 2-(2H-benzotriazol-2-yl)-6-(2-methylallyl)-4-methylphenol |
| E | 2-(5-methoxy-2H-benzotriazol-2-yl)-6-tert-butyl-4-(3-(methacryloyloxy)propoxy)phenol |
| F | 2-(5-methoxy-2H-benzotriazol-2-yl)-6-tert-butyl-4-(3-(vinyldimethylsilyl)propoxy)phenol |

TABLE 2

UV-Visible transmission data for solutions of benzotriazole compounds

| UV Absorber Compound | Molecular Wt. (MW), mg/mmole | Conc. (wt %) | Estimated Molar conc nmole/mL, M | Transmission cutoff Wavelength in nm 1% T | 10% T |
|---|---|---|---|---|---|
| A | 285.3 | 1.78 | 0.0926 | 391.0 | 395.0 |
| B | 341.4 | 1.73 | 0.0672 | 394.5 | 398.0 |
| C | 423.5 | 1.77 | 0.0620 | 397.0 | 400.5 |
| D | 279.3 | 1.74 | 0.0925 | 398.0 | 401.5 |
| 2 | 301.3 | 1.82 | 0.0896 | 410.0 | 414.5 |
| 1 | 453.5 | 1.73 | 0.0566 | 416.0 | 420.5 |
| 3 | 401.5 | 1.77 | 0.0654 | 417.5 | 421.5 |
| E | 439.5 | 1.73 | 0.0584 | 421.5 | 426.0 |
| E | 439.5 | 1.85 | 0.0625 | 422.0 | 426.5 |
| F | 411.5 | 1.81 | 0.0653 | 424.5 | 429.5 |

Example 3

Acrylic Lens Materials Containing Compound 1

A monomer diluent formulation consisting of 2-phenylethyl acrylate (PEA), 2-phenylethyl methacrylate (PEMA), and 1,4-butanediol diacrylate (BDDA) was prepared by mixing the three monomers together in the proportions of 65:30:3.2 parts by weight. Formulations containing 1.8, 2.4 and 3.0% of Compound 1 was prepared by dissolving 0.036, 0.048, 0.060 grams of Compound 1, weighed to an accuracy of ±0.01 mg, into the PEA/PEMA/BDDA monomer diluent to make 2 grams of each formulation. A comparison formulation containing 1.8% of ortho-methallyl Tinuvin P (Compound D) was prepared by dissolving 0.036 grams of Compound D into 1.968 grams of the PEA/PEMA/BDDA monomer diluent. Just prior to curing, to each formulation was added 1.8% bis-(4-tert-butylcyclohexylperoxy) dicarbonate (Perkadox-16, Akzo Corp.) initiator, by dissolving approximately 0.020 grams into each formulation (1.0%) and mixing on a vortex mixer. A control formulation that did not contain any UV absorber was prepared by dissolving 1.0% of the Perkadox 16 initiator into the PEA/PEMA/BDDA monomer diluent.

After mixing, each formulation was passed through a 0.45 μm membrane syringe filter and purged with nitrogen. Finally, each formulation was cast into polypropylene molds to form 1×2-cm×~1-mm rectangular films by thermal curing at 70° C. for 7 hours, followed by 7 hours at 100° C. in a programmable temperature oven (1000 Halfo Series, VWR Scientific Corp.). The films were demolded and 3 representative samples from each group were weighted and 2 were analyzed by UV-Visible transmission spectroscopy. The films were placed into polypropylene tissue capsules, Soxhlet extracted with acetone, and slowly dried in air and at 60° C. in a vacuum oven to remove residual acetone. After extraction and vacuum drying, the same film samples were weighed again and re-analyzed by UV-Visible transmission spectroscopy. The UV-Visible analysis was performed from 300-800 nm using a Perkin-Elmer Lambda 35 instrument equipped with a Lab Sphere RSA-PE-20 integrating sphere.

Figure 2:
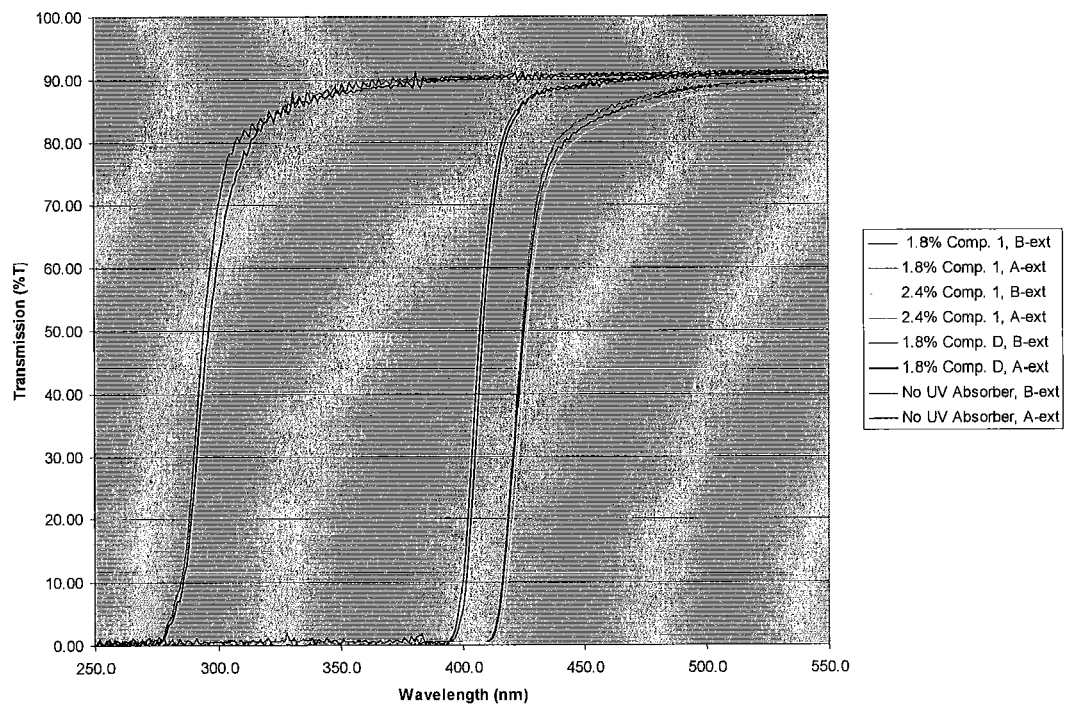
FIG. 2 shows the UV/VIS spectra of an acrylic IOL material containing the UV absorber of Example 1 (Compound 1) before and after extraction.

The UV absorber Compound 1 exhibited inhibitory character with the 3.0% formulation not curing to a solid material and increased extractables in going from 1.8 to 2.4% Compound 1 concentration (Table 3). Nonetheless, this experiment verified the presence of the polymerizable methacrylate group in the Compound 1 structure given the minimal change between the before and after extraction for the 1 and 10% transmission cutoff wavelengths in the 1.8 and 2.4% Compound 1 materials. In comparison to Compound D, Compound 1 shows very good incorporation into the acrylic lens material on free radical polymerization (Table 3). As well, the transmission spectra before and after extraction for these materials are nearly identical (FIG. 2).

TABLE 3

UV-Visible Transmission Cutoffs and Extractables for Compound 1 in Acrylic Lens Material Slabs Cured with 1.0% Perkadox 16

| UV Absorber Compound | Conc. Wt % | B/A Extraction | Wavelength (nm) for Transmission Cutoff 1% T | 10% T | % Total Extractables AVE | SD |
|---|---|---|---|---|---|---|
| 1 | 1.80 | Before | 412.0 | 416.5 | 1.18 | 0.431 |
|   |      | After  | 411.5 | 416.5 |      |       |
| 1 | 2.40 | Before | 413.5 | 418.5 | 4.21 | 2.068 |
|   |      | After  | 413.5 | 418.0 |      |       |
| 1 | 3.00 | Material did not cure | | | N/A | N/A |
| D | 1.80 | Before | 396.5 | 401.0 | 2.05 | 1.369 |
|   |      | After  | 395.5 | 400.0 |      |       |
| None | 0 | Before | 277.5 | 284.5 | 0.22 | 0.058 |
|   |      | After  | 278.0 | 285.5 |      |       |

We claim:

1. A UV absorber of the formula

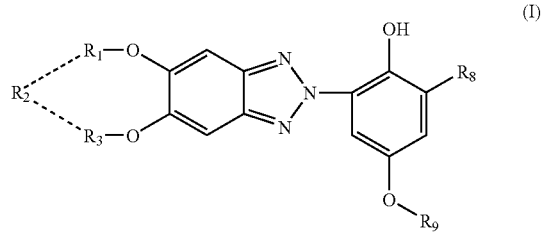

(I)

wherein $R_1$ and $R_3$ independently=H; $C_1$-$C_{12}$ alkyl, optionally substituted; $C_1$-$C_{12}$ cycloalkyl, optionally substituted; phenyl, optionally substituted; or naphthyl; or $R_1$ and $R_3$ are linked through the optional (as designated by the dashed bonds) linking group $R_2$ where $R_2$ is a $C_1$-$C_6$ alkylene, optionally substituted; or $R_1$, $R_2$, and $R_3$ taken together form an optionally substituted 1,2-phenyl, 1,2-naphthyl, or 2,3-naphthyl, wherein, in each case, the optional substituents are independently $C_1$-$C_6$ alkyl, $C_1$-$C_6$ alkoxy, OH, —Si(CH$_3$)$_3$, halogen, —(CH$_2$CH$_2$O)$_n$—R$_{10}$, or —(CH$_2$CH(CH$_3$)O)$_n$R$_{10}$;

$R_{10}$=H, —Si(CH$_3$)$_3$, or $C_1$-$C_6$ alkyl;

$R_8$=H or $C_1$-$C_{12}$ alkyl; and $R_9$=H; $C_1$-$C_{12}$ alkyl, optionally substituted with OH; or

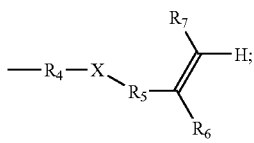

$R_4$=$C_1$-$C_{12}$ alkylene, (CH$_2$CH$_2$O)$_n$, (CH$_2$CH(CH$_3$)O)$_n$, or CH$_2$CH$_2$CH$_2$(Si(CH$_3$)$_2$O)$_m$Si(CH$_3$)$_2$CH$_2$CH$_2$CH$_2$;

X=nothing, O, NR$_7$, or S, provided that if $R_4$ is (CH$_2$CH$_2$O)$_n$, or (CH$_2$CH(CH$_3$)O)$_n$ then X is nothing;

$R_5$=nothing, C(=O), C(=O)C$_j$H$_{2j}$, $C_1$-$C_6$ alkylene, phenyl, or $C_1$-$C_6$ alkylphenyl; C(=O)O, C(=O)OC$_j$H$_{2j}$, C(=O)NR$_7$, C(=O)NR$_7$C$_j$H$_{2j}$, C(=S)O, C(=S)OC$_j$H$_{2j}$, C(=S)NR$_7$, C(=S)NR$_7$C$_j$H$_{2j}$, n=2-10;

j=1-6;

m=1-9;

$R_6$=H or methyl; and $R_7$=H, $C_1$-$C_6$ alkyl, or phenyl.

2. The UV absorber of claim 1 wherein $R_1$ and $R_3$ independently=$C_1$-$C_4$ alkyl or phenyl;

$R_2$=nothing;

$R_9$=

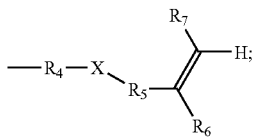

$R_4$ is $C_1$-$C_6$ alkylene;

X is O or NR$_7$;

$R_5$ is C(=O) or $C_1$-$C_6$ alkylphenyl;

$R_6$ is H or methyl;

$R_7$ is H; and $R_8$ is $C_4$-$C_{12}$ t-alkyl.

3. The UV absorber of claim 2 wherein:

$R_1$ and $R_3$=methyl;

$R_2$=nothing;

$R_9$=

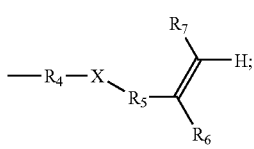

$R_4$ is $C_2$-$C_3$ alkylene;

X is O;

$R_5$ is C(=O), $R_6$ is H or methyl;

$R_7$ is H; and $R_8$ is t-butyl.

4. The UV absorber of claim 1 wherein the UV absorber is N-2-[2'-Hydroxy-3'-tert-butyl-5'-(3"-methacryloyloxypropoxy)phenyl]-5,6-dimethoxy-2H-benzotriazole.

5. An ophthalmic device material comprising the UV absorber of claim 1 and a device-forming monomer selected from the group consisting of acrylic monomers and silicone-containing monomers.

6. The ophthalmic device material of claim 5 wherein the ophthalmic device material comprises from 0.1 to 5% (w/w) of the UV absorber of claim 1.

7. The ophthalmic device material of claim 6 wherein the ophthalmic device material comprises from 0.1 to 2% (w/w) of the UV absorber of claim 1.

8. The ophthalmic device material of claim 5 wherein the ophthalmic device material comprises a device-forming monomer of formula [II]:

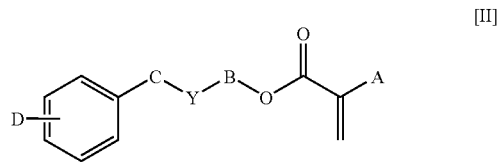

where in formula [II]:

A is H, CH$_3$, CH$_2$CH$_3$, or CH$_2$OH;

B is (CH$_2$)$_m$ or [O(CH$_2$)$_2$]$_z$;

C is (CH$_2$)$_w$;

m is 2-6;

z is 1-10;

Y is nothing, O, S, or NR', provided that if Y is O, S, or NR', then B is (CH$_2$)$_m$;

R' is H, CH$_3$, C$_n$H$_{2n'+1}$ (n'=1-10), iso-OC$_3$H$_7$, C$_6$H$_5$, or CH$_2$C$_6$H$_5$;

w is 0-6, provided that m+w≦8; and

D is H, $C_1$-$C_4$ alkyl, $C_1$-$C_4$ alkoxy, C$_6$H$_5$, CH$_2$C$_6$H$_5$ or halogen.

9. The ophthalmic device material of claim 8 wherein in formula [II]:

A is H or CH$_3$;

B is (CH$_2$)$_m$;

m is 2-5;

Y is nothing or O;

w is 0-1; and

D is H.

10. The ophthalmic device material of claim 9 wherein the ophthalmic device material comprises a monomer selected from the group consisting of: 2-phenylethyl methacrylate; 4-phenylbutyl methacrylate; 5-phenylpentyl methacrylate; 2-benzyloxyethyl methacrylate; and 3-benzyloxypropyl methacrylate; and their corresponding acrylates.

11. The ophthalmic device material of claim 5 wherein the ophthalmic device material comprises a cross-linking agent.

12. The ophthalmic device material of claim 5 wherein the ophthalmic device material comprises a reactive blue-light absorbing compound.

13. An intraocular lens comprising the UV absorber of claim 1.

14. An intraocular lens comprising the UV absorber of claim 2.

15. An intraocular lens comprising the UV absorber of claim 3.

16. An intraocular lens comprising the UV absorber of claim 4.

17. An ophthalmic device comprising the ophthalmic device material of claim 5.

18. The ophthalmic device of claim 17 wherein the ophthalmic device is selected from the group consisting of an intraocular lens; a contact lens; a keratoprosthesis; and a corneal inlay or ring.

* * * * *